United States Patent

Melzig et al.

[11] Patent Number: 5,952,515
[45] Date of Patent: Sep. 14, 1999

[54] DIARYL-2H-NAPTHOPYRANS

[75] Inventors: Manfred Melzig, Wessling; Herbert Zinner, Taufkirchen, both of Germany

[73] Assignee: Optische Werke G. Rodenstock, Munich, Germany

[21] Appl. No.: 08/765,734

[22] PCT Filed: Jul. 11, 1995

[86] PCT No.: PCT/DE95/00897

§ 371 Date: Jul. 30, 1997

§ 102(e) Date: Jul. 30, 1997

[87] PCT Pub. No.: WO96/01884

PCT Pub. Date: Jan. 25, 1996

[30] Foreign Application Priority Data

Jul. 11, 1994 [DE] Germany ............... 44 24 351

[51] Int. Cl.$^6$ ............ C07D 311/92; C07D 271/06; C07D 263/02; C07D 263/56
[52] U.S. Cl. ............ 549/389; 548/131; 548/215; 548/224
[58] Field of Search ............. 549/389; 548/131, 548/215, 224

[56] References Cited

U.S. PATENT DOCUMENTS

| | | | |
|---|---|---|---|
| 5,066,818 | 11/1991 | Gemert et al. | 549/389 |
| 5,238,981 | 8/1993 | Knowles | 524/110 |
| 5,340,857 | 8/1994 | Van Gemert | 524/110 |
| 5,369,158 | 11/1994 | Knowles | 524/110 |
| 5,458,814 | 10/1995 | Kumar et al. | 252/586 |
| 5,578,252 | 11/1996 | Van Gemert et al. | 252/586 |
| 5,623,005 | 4/1997 | Rickwood et al. | 524/96 |

*Primary Examiner*—Deborah C. Lambkin
*Attorney, Agent, or Firm*—Antonelli, Terry, Stout & Kraus, LLP

[57] ABSTRACT

The description concerns a photochromicsubstance, with a diaryl-2H-naphthopyrane having a link in the form Y—Ar, Z—Ar, Y—Ar—Y, Y—Ar—Y', Y—Ar—Z, Z—Ar—Z or Z—Ar—Z', in which Y, Y', Z and Z' are pyranes. The photochromic substance is also distinguished in that it has an aryl substituent which reduces the migration of the molecules in plastics.

8 Claims, No Drawings

DIARYL-2H-NAPTHOPYRANS

This application is a 371 of PCT/DE95/00897 Nov. 11, 1995.

TECHNICAL FIELD

The present invention relates to photochromic diaryl-2H-naphtopyrans.

STATE OF THE ART

Pyrans have been known as photochromic compounds for 25 years. One of the first descriptions of pyrans is in U.S. Pat. No. 3,567,605, in which the various benzo- and naphthopyrans including diphenyl-naphtopyrans are also described. However for years these compounds have remained uninteresting, because they only dye at very low temperatures (−40° C.).

Only recently have pyrans become known that also dye photochromically at normal temperatures and thus seem suited for use in ophthalmic lenses. Reference is made, by way of example, to U.S. Pat. No. 5,066,818, WO 93/10112 or WO 92/09593.

However, these known pyrans still have drawbacks with regard to their longevity and/or migration properties as well as their photochromic properties.

In particular, the material specific varying migration of the individual pyran compounds leads to inadequate dyeing results in surface coloring if these pyran compounds are utilized in mixtures, which are needed to obtain a desired mixed tone, because each individual compound penetrates to a different depth into the to-be-dyed material depending on the specific migration velocity.

The result are, comparable to the procedures in chromatography, layers in which the different pyran compounds are found in above average concentrations.

Moreover, the relatively great migration velocity of the compounds known from the state of the art results in a short lifetime of the dyed plastic objects. The known dyestuffs migrate relatively quickly out of the dyed object to its surface and cause separation phenomena there.

DESCRIPTION OF THE INVENTION

The object of the present invention is to provide substances, which dye photochromically well at room temperature, lighten up quickly enough for ophthalmic lenses, possess sufficient longevity and due to their spatial structure have less tendency to migrate than the compounds known from the state of the art, and to describe the synthesis of these substances.

An invented solution to this object is set forth in claims 1 and 2.

Further improvements of the present invention are the subject matter of the dependent claims.

The subject matter of the present invention are therefore photochromic compounds having a diaryl-2H-naphthopyran-structure, which possesses an advantageous substitution at its aryl substituents.

On the one hand, this substitution of the aryl substituents comprises linking the naphthopyran-structure to the first starting compound described in claim 2 under a) by means of the invented process, with which 'monomeric' diaryl-2H-naphthopyrans which possess one photochromically reacting center are produced.

On the other hand, the photochromic substance yielded by the described process possesses an especially advantageous substitution of the aryl substituents if the aryl substituent of the diaryl-2H-naphthopyran compound is linked via the starting compound described in claim 2 under a) to at least one other diaryl-2H-naphthopyran compound.

Dependent on the selection of the starting compound

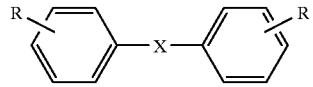

the photochromic substance possesses a link of at least two photochromic partial systems, which either are characterized by an electron-conducting bridge or by a bridge that interrupts electron delocalization.

An element of the present invention is that it was understood that a solution to the object can succeed in a very simple manner by substituting the aryl substituents of the diaryl-2H-naphthopyran compounds known from the state of the art in a suitable manner.

All the photochromic properties such as color, darkening and lightening up velocity, temperature dependency and longevity of the photochromic reaction are retained; at the same time the invented compounds show distinctly less tendency to migrate than the compounds known from the state of the art.

Moreover, various diaryl-2H-naphthopyrans can be linked in this way. This has the advantage that several dyestuffs of varying absorption possess identical ability to migrate in an excited state or in an unexcited state, because they are located in a whole molecule. In this manner, various problems that occur with a variety of dyestuffs particularly in surface coloring can be elegantly avoided.

DESCRIPTION OF THE PREFERRED EMBODIMENTS

The present invention is made more apparent in the following using preferred embodiments.

First the synthesis of the photochromic substances is described:

1. Production of the starting products for synthesis of a ketone according to claim 2a):

The synthesis of the invented substances is based on a diaryl compound. This compound may be a diarylalkane and/or a diarylether from the homologous series described in claim 2a).

a) Synthesis of the Diarylalkanes:

The short-chained homologues of this starting compound, biphenyl, diphenylmethane and dibenzyl (n=0, 1, 2), are commercially available, for example from Aldrich (No. 14410, 43100).

The simplest way to produce the starting compound 1,3-diphenylpropane (n=3) by means of the Clemmensen reduction of a commercial dibenzylketone.

For this purpose, 30 g of zinc dust, 2.5 g of $HgCl_2$, 1.5 ml of conc. HCl and 38 ml of water are shook for five minutes. The top most fluid is decanted, to the formed amalgam are then added 20 ml of water, 45 ml of conc. HCl, 25 ml of toluene and 14.7 g of dibenzylketone. This mixture is heated for 24 hours while recycling and every 5 hours 12.5 ml of concentrated HCl is being added. After cooling, the organic phase is separated, the aqueous phase is diluted with 50 ml of water and extracted 3 times with 50 ml of ether. The ether phases are combined and shook out with 50 ml of water, and then dried over $Na_2SO_4$. After withdrawal of the ether, the starting compound 1.3-diphenylpropane is left in the form of a colorless oil.

Hydrogenation of the commercially available 1,4-diphenyl-1,3-butadiene is suited for producing the next higher homologue with n=4, 1,4-diphenylbutane. For this purpose, 21.5 g of 1,4-diphenyl-1,3-butadiene is suspended in 400 ml of pure acetic acid and mixed with 8 g of palladium carbon, corresponding to about 0.5 g of palladium, while passing in $H_2$ gas. The hydrogenation has ended when the butadiene has completely dissolved and the weak violet fluorescence has extinguished. After percolation, the filtrate is mixed with water until it becomes cloudy and heated for 10 minutes to 85° C. Then it is cooled and shook out with toluene. The toluene phase is dried over $Na_2SO_4$, the solvent is removed and the residue is distilled. During distillation the desired starting compound, 1,4-diphenylbutane, turns into a colorless oil which already congeals to a white mass in the recipient vessel. The melting point is at 52° C.

For the production of 1,5-diphenylpentane (n=5), the compound 1,5-diphenyl-1,4-pentadiene-3-on, which can be obtained from Aldrich under the number 43143, is hydrogenated. For this purpose 50 g of ketone are mixed with 16 g of palladium carbon in 500 ml of acetone at a reaction temperature of 15° C. During the automatically occurring hydrogenation while passing in $H_2$ gas, the top most fluid turns light yellow. After hydrogenation has ended, it is filtered. The solvent is removed from the filtrate and the residue is then distilled. At 185° C. and a pressure of 2666 Pa, the desired compound, 1,5-diphenylpentane, turns into a colorless oil. The yield is practically quantitative.

Suited for the production of the starting compound with n=6, 1,6-diphenylhexane, by the way of example, is hydrogenation of 1,6-phenylhexatriene. For this purpose 24 g of diphenyl-hexatriene, which can be obtained from Aldrich under the number 43050, is suspended in 400 ml of pure acetic acid and mixed with 8 g of palladium carbon, which corresponds to about 0.5 g of palladium. The $H_2$ is passed in until the triene has completely dissolved and the blue fluorescence has extinguished. After percolation, the filtrate is mixed with water until it becomes cloudy and heated for 10 minutes to 85° C. During this a colorless oil separates at the top, which is distilled after separation. The starting compound, 1,6-diphenylhexane, desired for the synthesis of the invented substances turns into a colorless oil during distillation at 208° C. and at a pressure of 2666 Pa. This colorless oil does not easily congeal. The white crystals obtained from the ethanol have a melting point of 136 to 137° C.

b) Synthesis of the Diarylethers:

The symmetrical diarylethers, such as diphenylether (m=n=0) and dibenzylether (m=n=-1) can be obtained from Aldrich under the numbers 42730 and 33630, employed for the synthesis of the invented photochromic substance having a diaryl-2H-naphtopyran structure. The representation of the diphenethylether (m=n=2) occurs according to the information in Jain et al., J. Ind. Chem. Soc. 28(1951), 49; of bis-(3-phenylpropyl)-ether (m=n=3) can be produced according to directions in A. Morton et al., J.A.C.S. 63 (1941) 326.

Also unsymmetrical ethers which are also suited as a starting compound can be easily represented by the synthesis described in the following.

For the production of benzylphenethylether (m=1, n=2), 23 g of the finest Na wire is suspended in 350 ml of toluene. Then, while stirring well, 122 g of phenethylalcohol is added dropwise. During this addition, the mixture is heated to boiling, after about 1 hour gas stops developing. After then adding 126 g of benzylchloride, it is boiled another 90 minutes while recycling. Then it is cooled and mixed with water. The organic phase is separated from the two resulting phases, washed with water, dried and fractionally distilled. During distillation the benzylphenethylether to be employed as the starting compound for the synthesis of the photochromic substance turns into a colorless oil at about 180° C. and 1733 Pa.

c) Synthesis of the Diaryl Compounds Substituted at the Aryl Remainder:

For the production of 1-phenyl-3-(3,4,5-trimethoxyphenyl-)propane as the starting product for the synthesis of the photochromic substance having a diaryl-2H-naphthopyran structure, 81 g of 3,4,5-trimethoxybenzaldehyde, 49 g of actophenone, 150 ml of ethanol and 150 ml of 10% NaOH are stirred for 4 hours at room temperature. The aldehyde and the phenone can be obtained from Aldrich under the numbers 92140 and 00790. After cooling down to 5° C., the precipitated yellow ethanol crystals (MP 131° C.) are recrystallized. 60 g of this product are suspended in 400 ml of ethylacetate, mixed with 30 g of palladium carbon as a catalyst and 4 ml of 70% perchloric acid and hydrogenized in an autoclave while stirring for 30 hours with 2.5 bar $H_2$. The mixture is filtered and the filtrate is then distilled. At a pressure of 66.6 Pa and at 180 to 196° C., the synthesized product, 1-phenyl-3-(3,4,5-trimethoxyphenyl-)propane, turns into a colorless oil.

Due to the great number of commercially available substituted benzaldehydes and acetophenones as well as the easy conduction and high yield of the described reaction (usually 70%), this procedure is also conceivable for all the other, not explicitly described here, starting compounds for the synthesis of the invented substance.

For the synthesis of the diarylethers substituted in the aryl part, equimolar amounts of benzylchloride or benzylbromide, which can be substituted in a suitable manner, and phenol with an equimolar amount of sodium-ethylate are boiled in 5% ethanol in a waterbath until the reaction solution has become neutral. The product can precipitate by itself; If this is not the case, the alcohol has to be removed to force the precipitation.

Finally it is filtered out, rewashed with water and recrystallized. If, due to the substitution of the benzylchloride, -bromide or of the phenol, one obtains an oily product, the neutral reaction solution is strongly diluted with water and shook out with ether. The yielded ether extract is washed with diluted 2% NaOH, dried over $Na_2SO_4$ and the solvent is removed. In the event that the product still has an oily consistency after this treatment, it undergoes fractional distillation in high vacuum (133 to 67) Pa.

If, for example, 2,4-dibromphenol, which can be obtained from Aldrich, No. 34270, is made to react with benzylbromide and an equimolar amount of sodium ethylate in 5% ethanol, 2,4-dibromphenylbenzylether is yielded. Following recrystillization from ethanol/water, colorless glossy needles are yielded with a melting point of 68° C.

The substituted diarylether, 2,3,5-trimethylphenylbenyl-ether, can be produced by making 2,3,5-trimethylphenol react with benzylbromide under the abovementioned conditions. In this case, flat colorless prisms with a melting point of 450° C. are yielded after recrystillization.

2. Synthesis of the Ketones According to claim 2a):

a) Synthesis of 1,2-di(4-benzophenonyl-)ethane and 4-phenethylbenzophenone:

168.8 g (1.20 mol) of benzoychloride are added to 181.4 g (1.36 mol) of anhydrous $AlCl_3$, in 400 ml of 1,2- dichlorethane while stirring at room temperature. This suspension becomes darker with the dissolution of the aluminium salt. While it is cooled weakly, 100 g (0,56 mol) of dibenzyl is added at <20° C. The dark brown solution is stirred for 1 more hour and left to stand over night.

The reaction mass is carefully poured onto 400 g of ice and acidified with HCL. The organic phase is separated, shaken out with 2% NaOh and dried with sodium sulfate. After filtering, the dichlorethane is removed. Yielded are 160.1 g of an orange oil, which is composed in addition to some starting product of 82% of 1,2-di(4-benzophenone)-ethane and 14% of 4-phenethyl-benzophenone.

b) Synthesis of a Ketone Substituted in the Aryl Part:

62 g of benzoyl chloride are added to 66 g of anhydrous AlCl₃ in 100 ml of carbon disulfide while stirring well with absolute exclusion of moisture. Subsequently, 30 g of dimethylaminophenyl are added to 300 ml of carbon disulfide and the reaction mixture is boiled for 15 hours while recycling. The reaction mass is then poured carefully onto ice and acidified with HCl. The organic phase is separated and mixed with NaOH. The resulting precipitated product is filtered off and recrytallized from ethylmetyl ketone. After recrystallization, melting point flakes with a melting point of 180° C. are yielded.

yellow solution is heated while stirring to 60° C. After adding a spatula tip of 4-toluenesulfonic acid it darkens fast. In UV light, the paper sample immediately yields orange photochromy. The solution is stirred for 1 more hour at 60° C. After removing the toluene, the remaining green oil is absorbed in ethanol, brought briefly to a boil and left to stand over night. After separation of the undissolvable, the ethanol is removed and the remainder is chromatographed over aluminium oxide with methylene chloride. Of the 4 created orange photochromy compounds (DC control), only the 2 in the first fraction are collected. 66 g of an orange oil are left after removing the solvent. After a few days this oil crystallizes to a yellow crystalline mass. After washing with methanol, this crystalline mass can be used to dye plastic lenses. Fractionized crystallization (dissolving the crystals in diethylether and partial precipitation with ethanol; procedure repeated several times) permits obtaining the two photochrome compounds separately.

According to the NMR analysis, the greater part is composed of:

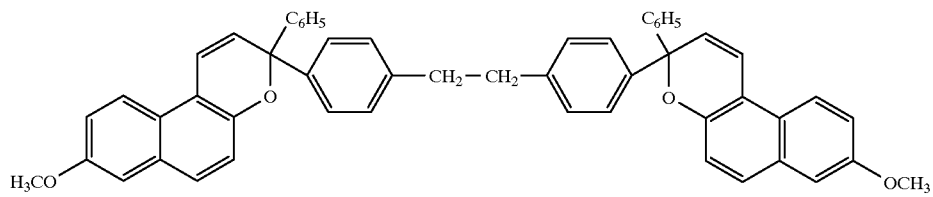

c) Synthesis of a Ketone from a Diarylether:

A diarylether yielded under 1. b) is placed at about 10 to 15° C. in 1,2-dichloroethane. Subsequently 180 g of anhydrous AlCl₃ and 170 g of benzoyl chloride are added dropwise to 400 ml of 1,2-dichloroethane.

The, for Friedel-Crafts acylation, unusually low excess ALCl₃ must be strictly maintained in the case of the above-described conversion of diarylether with aryl carbonic acid halides, because otherwise ether splitting will easily occur.

Ether splitting occurs to a much smaller degree if methoxy groups or ethoxy groups are introduced via the aryl remainder of the acid halides so that these ketones can be produced without difficulty.

3. Synthesis of the Tertiary Alcohol Respectively Carbinol:

160 g of the mixture of 2. a) are dissolved in 350 ml of dried dimethyl sulfoxide while stirring and slowly added to 78 g of lithium acetylide ethylene diamine complex. The dark brown solution is stirred for 62 hours at room temperature and turns deep red. It is carefully poured onto 800 g of ice and immediately acidified with 2n of HCl. The reaction mass is extracted with ether in a liquid-liquid extractor until the etherphase is completely colorless. After drying the ether with sodium sulfate, filtering occurs, the ether is removed from the filtrate. Left are 171.4 g of an orange oil, which consolidates to a yellow crystal mass after standing for a while. 74% of this mass is 4,4'-di(1-hydroxy-1-phenyl-prop-3-in-1-yl)dibenzyl and 13% of it is 3-phenyl-3-(4-phenethyl)phenyl-prop-1-in-3-ol.

4. Synthesis of the Photochromic Compounds:

109 g of the mixture of 3. is dissolved in 500 ml toluene and added to 73,2 g of 6-methoxy-2-naphthol. The dark The second compound is identified as a 'monomeric' photochromic substance having the following structure:

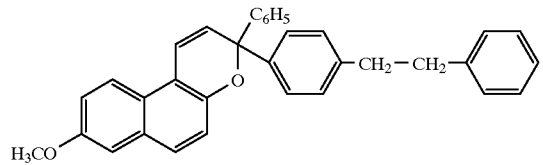

Comparison of the invented photochromic substances with the state-of-the-art substances:

According to the synthesis instructions set forth in 1. to 4. , the invented substances are produced according to the following structure formula with the designated remainders:

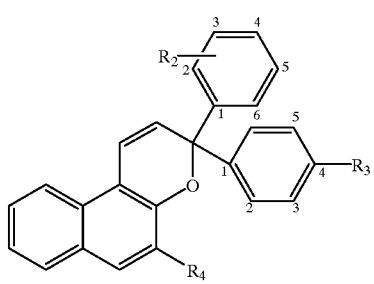

Thus the present invention includes photochromic substances having a diaryl-2-H-naphthopyran structure, characterized by it possessing an aryl substituent which reduces the molecule migration in plastics, obtained by: a) Synthesis of a ketone from a diaryl alkane and/or a diarylether and a halogenated arylcarbonic acid by Friedel Crafts' acylation according to the following reaction diagram:

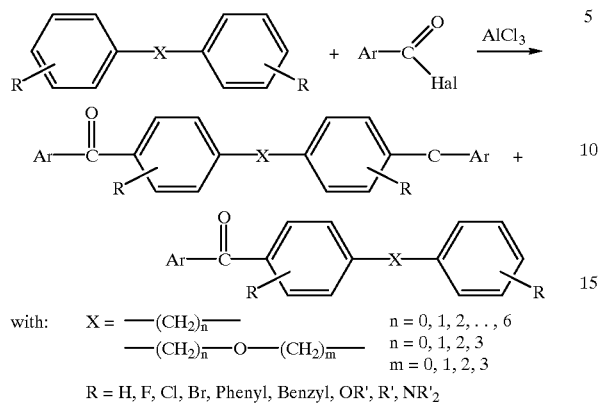

with:  $X = -(CH_2)_n-$    $n = 0, 1, 2, \ldots, 6$
       $-(CH_2)_n-O-(CH_2)_m-$   $n = 0, 1, 2, 3$
                                  $m = 0, 1, 2, 3$ R = H, F, Cl, Br, Phenyl, Benzyl, OR', R', NR'$_2$ R'=alkyl with up to 6 C-atoms or cycloalkyl with 5 or 6 C-atoms

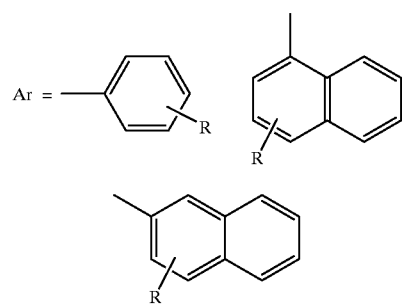

b) Synthesis of a tertiary alcohol having carbon-carbon-triple links from the ketone yielded by a) and a metal acetylide by means of nucleophilic addition; c) Synthesis of the photochromic substance by means of condensation of said tertiary alcohol with a substituted diarylalcohol according to the following reaction diagram:

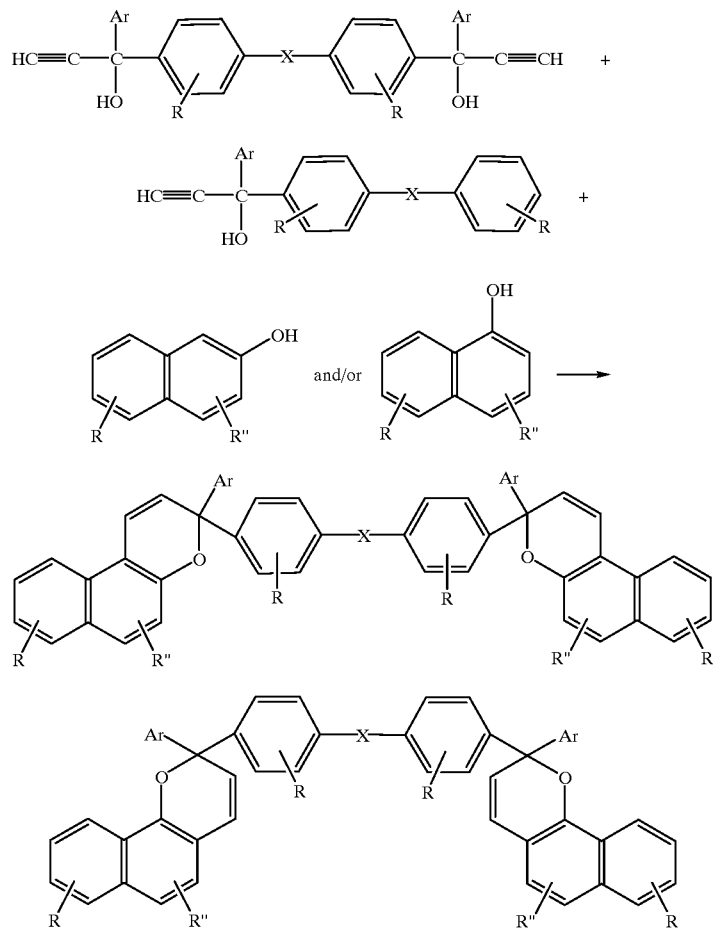

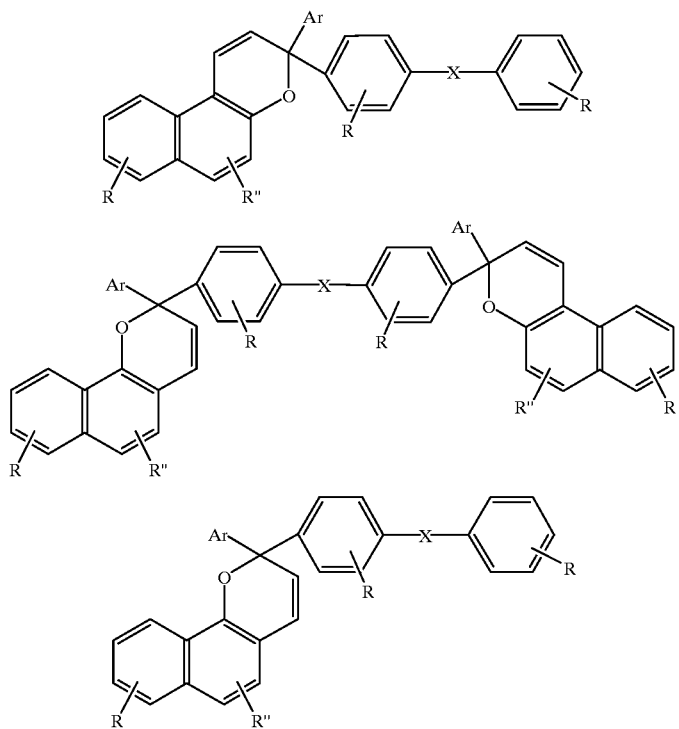
with: X, Ar, R, R' as under a)
R" = H, F, Cl, Br, R', OR', O—C(=O)—C$_6$H$_5$, O—C(=O)—R'
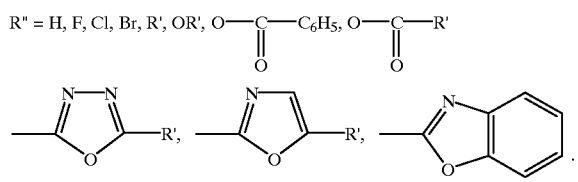
TABLE 1
| Example No. | R$_1$ | R$_2$ | R$_3$ |
|---|---|---|---|
| 1 | H | H | —CH$_2$—CH$_2$—C$_6$H$_5$ |
| 2 | H | H | 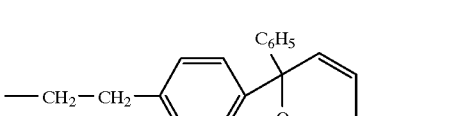 |
| 3 | H | H | —(CH$_2$)$_6$—C$_6$H$_5$ |

TABLE 1-continued

| Example No. | R₁ | R₂ | R₃ |
|---|---|---|---|
| 4 | H | H | —(CH₂)₆—[4-(3-phenyl-3H-naphtho[2,1-b]pyran-3-yl)phenyl] |
| 5 | H | H | —CH₂—O—CH₂—C₆H₅ |
| 6 | H | H | —CH₂—O—CH₂—[4-(3-phenyl-3H-naphtho[2,1-b]pyran-3-yl)phenyl] |
| 7 | H | H | —(CH₂)₃—(3,4,5-trimethoxyphenyl) |
| 8 | H | H | —(4-(N,N-dimethylamino)phenyl) |
| 9 | H | H | —CH₂—O—(2,4-dibromophenyl) |
| 10 | H | H | —CH₂—O—(2,3,5-trimethylphenyl) |
| 11 | H | 4-CH₃ | —(CH₂)₃—C₆H₅ |
| 12 | H | 4-OCH₃ | —(CH₂)₃—C₆H₅ |
| 13 | H | 2-CH₃, 4-OCH₃ | —(CH₂)₃—(3,4,5-trimethoxyphenyl) |
| 14 | —O—C(=O)—CH₃ | H | —CH₂—CH₂—C₆H₅ |

TABLE 2

(reference substances):

| | $R_1$ | $R_2$ | $R_3$ | |
|---|---|---|---|---|
| Reference 1 | —O—C(=O)—CH$_3$ | 4-CH$_3$ | —CH$_3$ | Example 9 from US 5 340 857 |
| Reference 2 | H | 2-CH$_3$, 4-OCH$_3$ | —OCH$_3$ | Example 3 from US 5 066 818 |
| Reference 3 | H | 2-OCH$_3$, 4-OCH$_3$ | H | Example 5 from US 5 066 818 |

With the obtained substances and the three state-of-the art reference substances, ten surface-dyed and ten super dereflected CR 307 lenses (registered trade mark belonging to PPG Industries) were produced.

In order to evaluate the migration behavior of the photochromic substances and of the reference substances, these were examined after a specific number of boiling cycles of 2 minutes each in a 4% NaCl solution to determine at which number of the original ten lenses there are signs of the dyeing and the dereflection separating after the designated boiling cycle.

This separation, which is characterized by the photochromic substances which were introduced by the surface dyeing migrating to the surface of the dyed object and subsequently peeling off, occurs quicker with photochromic substances with stronger migration properties, because the migration velocity is greater.

TABLE 3

| Example No | \| | \| | \| | \| | Number of Boiling Cycles | \| | \| | \| | \| | \| |
|---|---|---|---|---|---|---|---|---|---|---|---|
| | 1 | 2 | 3 | 4 | 5 | 6 | 7 | 8 | 9 | 10 | >10 |
| 1 | — | — | 2 | 3 | 3 | 2 | | | | | |
| 2 | — | — | — | — | 1 | 3 | 2 | 2 | 1 | — | 1 |
| 3 | — | — | — | 3 | 2 | 2 | 2 | | | | |
| 4 | — | — | — | — | 1 | 2 | 1 | 3 | — | 1 | 2 |
| 5 | — | — | 2 | 2 | 4 | 1 | 1 | | | | |
| 6 | — | — | — | — | 2 | 2 | 1 | 2 | 1 | — | 2 |
| 7 | — | — | — | 1 | 3 | 3 | 1 | 1 | 1 | | |
| 8 | — | — | 2 | 4 | 2 | 2 | | | | | |
| 9 | — | — | 1 | 2 | 3 | 3 | 1 | | | | |
| 10 | — | — | 1 | 3 | 4 | 2 | | | | | |
| 11 | — | — | — | — | 1 | 1 | 2 | 2 | 2 | — | 2 |
| 12 | — | — | — | — | 1 | — | 2 | 3 | 3 | — | 1 |
| 13 | — | — | — | — | 2 | 3 | 3 | — | 1 | 1 | |
| 14 | — | — | 2 | 4 | 2 | 1 | 1 | | | | |
| 15 | — | — | — | 2 | 3 | 3 | 1 | 1 | | | |
| Vergleich Nr. | | | | | | | | | | | |
| 1 | — | 3 | 4 | 2 | 1 | | | | | | |
| 2 | — | 1 | 3 | 3 | 2 | 1 | | | | | |
| 3 | 1 | — | 4 | 2 | 3 | | | | | | |

These examples show that the objects dyed with the invented substances do not indicate signs of separation until after a greater number of boiling cycles. None of the lenses dyed with the example substance 1 to 15 showed these signs of coming off after the first two two-minute boiling cycles in 4% Na Cl solution caused by a greater migration velocity. Of the lenses dyed with the reference substances 1 to 3, one showed signs of separation after the first boiling cycle, four of the lenses (three with reference No. 1 and one with reference No. 2) already showed signs of separation after the second cycle.

What is claimed is:

1. A photochromic diaryl naphthopyran having the formula:

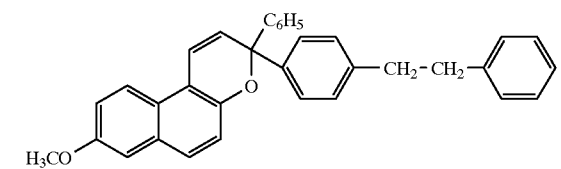

2. A photochromic diaryl naphthopyran having the formula:

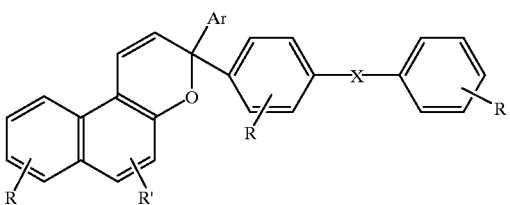

wherein R is selected from H, F, Cl, Br, Phenyl, Benzyl, —OR'; R', NR'$_2$;

wherein R' is an alkyl with up to 6 carbon atoms, or a cycloalkyl with 5 or 6 carbon atoms;

wherein R" is

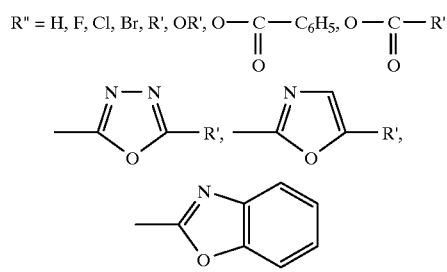

wherein Ar is

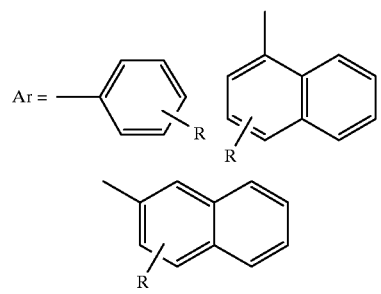

wherein X is a bridge that interrupts electron delocalization and X is selected from the group consisting of —(CH$_2$)$_n$— wherein n is an integer from 0 to 6; and —O—(CH$_2$)$_m$— wherein n and m are integers from 0 to 3.

3. A photochromic compound according to claim 2, wherein X=—(CH$_2$)$_n$—, wherein n is 2.

4. A photochromic compound according to claim 2, wherein Ar=

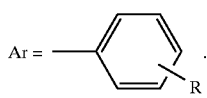

5. A photochromic diaryl naphthopyran having the formula:

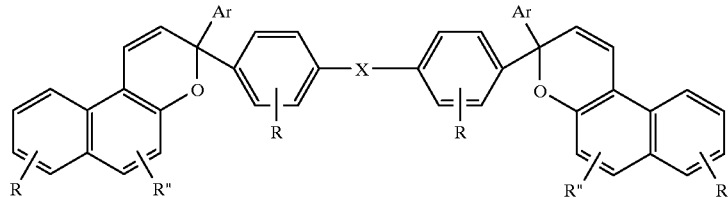

wherein R is selected from H, F, Cl, Br, Phenyl, Benzyl, —OR'; R', NR'2;
wherein R' is an alkyl with up to 6 carbon atoms, or a cycloalkyl with 5 or 6 carbon atoms;
wherein R" is

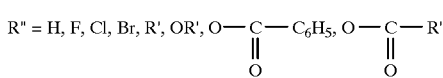

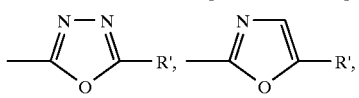

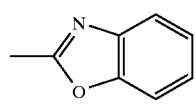

wherein Ar is

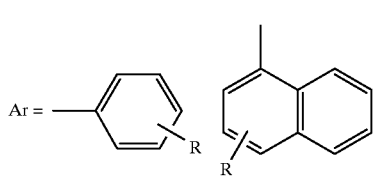

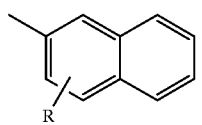

wherein X is a bridge that interrupts electron delocalization and X is selected from the group consisting of —(CH$_2$)$_n$— wherein n is an integer from 0 to 6; and —(CH$_2$)$_n$—O—(CH$_2$)$_m$— wherein n and m are integers from 0 to 3.

6. A photochromic compound according to claim 5, wherein Ar=

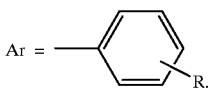

7. A photochromic diaryl naphthopyran according to claim 2, wherein n=0.

8. A photochromic diaryl naphthopyran according to claim 5, wherein n=0.

* * * * *